(12) United States Patent
Tang et al.

(10) Patent No.: US 11,995,824 B2
(45) Date of Patent: May 28, 2024

(54) SYSTEMS AND METHODS FOR DETERMINING CORRECTION PARAMETERS FOR IMAGING DEVICES

(71) Applicant: SHANGHAI UNITED IMAGING HEALTHCARE CO., LTD., Shanghai (CN)

(72) Inventors: Songsong Tang, Shanghai (CN); Yong Zhao, Shanghai (CN); Xin Fan, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 379 days.

(21) Appl. No.: 17/595,142

(22) PCT Filed: May 7, 2020

(86) PCT No.: PCT/CN2020/089030
§ 371 (c)(1),
(2) Date: Nov. 10, 2021

(87) PCT Pub. No.: WO2020/228587
PCT Pub. Date: Nov. 19, 2020

(65) Prior Publication Data
US 2022/0198656 A1    Jun. 23, 2022

(30) Foreign Application Priority Data
May 10, 2019  (CN) .......................... 201910390320.5

(51) Int. Cl.
G06T 7/00   (2017.01)
A61B 6/03   (2006.01)
A61B 6/42   (2024.01)

(52) U.S. Cl.
CPC ............ *G06T 7/0012* (2013.01); *A61B 6/037* (2013.01); *A61B 6/4208* (2013.01); *G06T 2207/10104* (2013.01)

(58) Field of Classification Search
CPC .................... G06T 7/0012; G06T 2201/10104
See application file for complete search history.

(56) References Cited

U.S. PATENT DOCUMENTS

2001/0040219 A1* 11/2001 Cherry ................. G01T 1/2985
                                                          250/363.03
2004/0084625 A1    5/2004 Williams et al.
(Continued)

FOREIGN PATENT DOCUMENTS

CN    102769510 A    11/2012
CN    106618618 A     5/2017
(Continued)

OTHER PUBLICATIONS

First Office Action in Chinese Application No. 201910390320.5 dated Dec. 29, 2020, 12 pages.
(Continued)

*Primary Examiner* — Kevin Ky
(74) *Attorney, Agent, or Firm* — METIS IP LLC

(57) ABSTRACT

Systems and methods for determining at least one correction parameter for a Positron Emission Tomography (PET) scanner including a plurality of detector units is provided. For each of the plurality of detector units, the methods may include determining, based on scan data of one or more scans of a phantom at a plurality of positions, a first sum of coincidence events detected by the detector unit. The methods may further include determining a second sum of coincidence events that are expected to be detected by the detector unit and determining, based on the first sum of coincidence events and the second sum of coincidence events, at least one correction parameter associated with the (Continued)

detector unit. The phantom may be moved to the plurality of positions along an axis of a field of view of the PET scanner during the one or more scans.

20 Claims, 9 Drawing Sheets

(56) References Cited

U.S. PATENT DOCUMENTS

| | | | |
|---|---|---|---|
| 2007/0176087 A1 | 8/2007 | Wang et al. | |
| 2011/0135179 A1 | 6/2011 | Ross et al. | |
| 2012/0290519 A1* | 11/2012 | Fontaine | G01T 1/2985 |
| | | | 250/252.1 |
| 2016/0131774 A1* | 5/2016 | Lage | A61B 6/5217 |
| | | | 600/425 |
| 2017/0345189 A1* | 11/2017 | Liu | A61B 6/0487 |
| 2018/0114345 A1* | 4/2018 | Liu | G06T 11/005 |
| 2018/0203141 A1* | 7/2018 | Chang | G06T 11/005 |
| 2020/0033491 A1* | 1/2020 | Panin | G01T 7/005 |
| 2020/0041669 A1 | 2/2020 | Dong | |
| 2022/0198656 A1* | 6/2022 | Tang | G06T 7/0012 |

FOREIGN PATENT DOCUMENTS

| | | |
|---|---|---|
| CN | 107049352 A | 8/2017 |
| CN | 107110988 A | 8/2017 |
| CN | 108209958 A | 6/2018 |
| CN | 109965897 A | 7/2019 |
| JP | 2011075419 A | 4/2011 |
| WO | 2020125710 A1 | 6/2020 |

OTHER PUBLICATIONS

International Search Report in PCT/CN2020/089030 dated Jul. 30, 2020, 5 pages.

Written Opinion in PCT/CN2020/089030 dated Jul. 30, 2020, 6 pages.

* cited by examiner

800

For each of the plurality of positions, determining an expected count of coincidence events based on geometric parameters of the phantom, position information of the phantom, and a scanning period of the phantom at the position ~ 802

Determining the reference sum of coincidence events based on the expected count of coincidence events for each of the plurality of positions ~ 804

FIG. 8

SYSTEMS AND METHODS FOR DETERMINING CORRECTION PARAMETERS FOR IMAGING DEVICES

CROSS-REFERENCE TO RELATED APPLICATIONS

The application is a U.S. national stage under 35 U.S.C. § 371 of International Application No. PCT/CN2020/089030. filed on May 7, 2020, designating the United States of America, which claims priority to Chinese Patent Application No. 201910390320.5 filed on May 10, 2019, the entire contents of each of which are hereby incorporated by reference.

TECHNICAL FIELD

The present disclosure generally relates to imaging devices, and more particularly, relates to systems and methods for determining one or more correction parameters for imaging devices, such as a Positron Emission Tomography (PET) scanner.

BACKGROUND

Positron Emission Tomography (PET) is a noninvasive nuclear medical imaging technique that is widely used for diagnostic analysis. In order to decrease artifacts in a PET image, there is a need for a normalization correction for the detection efficiency of detectors in the PET system and the detection efficiency of lines of response (LORs) of the detectors. In existing methods for normalization correction, a phantom is often used. The length of the phantom needs to cover the axial field of view (FOV) of the PET scanner so that gamma light of approximately the same intensity is emitted and then measured by the detectors. For a PET scanner with a relatively long axial FOV (e.g., such as a whole-body PET scanner that has an axial FOV of or close to 2 meters), a relatively long phantom is needed. There may be problems in transporting and/or storing such a long phantom. Moreover, it may be inconvenient for an operator to maneuver such a long phantom in a scanning of the phantom using the PET scanner. Furthermore, it may be difficult to manufacture a phantom of such a length. Therefore, it is desired to develop more convenient systems and methods for determining one or more correction parameters for PET scanners.

SUMMARY

According to an aspect of the present disclosure, a system for determining at least one correction parameter for a Positron Emission Tomography (PET) scanner including a plurality of detector units is provided. The system may include at least one non-transitory storage medium including a set of instructions and at least one processor in communication with the at least one non-transitory storage medium. When executing the set of instructions, for each of the plurality of detector units, the at least one processor may be configured to cause the system to perform operations including: determining, based on scan data of one or more scans of a phantom at a plurality of positions, a first sum of coincidence events detected by the detector unit. The phantom may be moved to the plurality of positions along an axis of a field of view of the PET scanner during the one or more scans, and a length of the phantom may be less than a length of the field of view of the PET scanner along the axis. The operations may further include determining a second sum of coincidence events that are expected to be detected by the detector unit, and determining, based on the first sum of coincidence events and the second sum of coincidence events, at least one correction parameter associated with the detector unit.

In some embodiments, to determine the first sum of coincidence events, the at least one processor may be configured to cause the system to perform operations including: obtaining the scan data of the one or more scans of the phantom at the plurality of positions; for each of the plurality of positions, determining, based on the scan data, a first count of detected coincidence events that are detected by the detector unit; and determining the first sum of coincidence events based on the first count of detected coincidence events for each of the plurality of positions.

In some embodiments, to determine the second sum of coincidence events, the at least one processor may be configured to cause the system to perform operations including: for each of the plurality of positions, determining a second count of coincidence events that are expected to be detected by the detector unit based on geometric parameters of the phantom, position information of the phantom, and a scanning period of the phantom at the position; and determining the second sum of coincidence events based on the second count of coincidence events for each of the plurality of positions.

In some embodiments, the phantom may be moved to the plurality of positions in a step-wise mode, and a moving distance for each movement of the phantom may be less than the length of the phantom.

In some embodiments, the phantom may be continuously moved to the plurality of positions.

In some embodiments, the phantom may be continuously moved to the plurality of positions at a constant speed.

In some embodiments, to determine the first sum of coincidence events, the at least one processor may be configured to cause the system to perform operations including performing one or more corrections on the scan data of the one or more scans of the phantom at the plurality of positions to obtain corrected scan data; and determining the first sum of coincidence events based on the corrected scan data. The one or more corrections may include at least one of an attenuation correction, a dead-time correction, a random coincidence correction, or a scatter correction.

In some embodiments, the at least one correction parameter may include an axial block profile, and to determine the at least one correction parameter, the at least one processor may be configured to cause the system to perform operations including determining the axial block profile associated with the PET scanner based on the first sum of coincidence events and the second sum of coincidence events.

In some embodiments, the at least one correction parameter may include a plane efficiency, and to determine the at least one correction parameter, the at least one processor may be configured to cause the system to perform operations including: obtaining a first corrected sum of coincidence events by correcting the first sum of coincidence events using the axial block profile for each detector unit, and determining the plane efficiency associated with the PET scanner based on the first corrected sum of coincidence events and the second sum of coincidence events.

In some embodiments, the at least one correction parameter may include a transverse block profile, and to determine the at least one correction parameter, the at least one processor may be further configured to cause the system to perform operations including obtaining a second corrected sum of coincidence events by correcting the first corrected sum of coincidence events using the plane efficiency for each detector unit, and determining the transverse block profile associated with the PET scanner based on the second corrected sum of coincidence events and the second sum of coincidence events.

In some embodiments, the at least one correction parameter may include a crystal efficiency, and to determine the at least one correction parameter, the at least one processor may be configured to cause the system to perform operations including: obtaining a third corrected sum of coincidence events by correcting the second corrected sum of coincidence events using the transverse block profile for each detector unit, and determining the crystal efficiency associated with the PET scanner based on the third corrected sum of coincidence events and the second sum of coincidence events.

According to another aspect of the present disclosure, a method for determining at least one correction parameter for a Positron Emission Tomography (PET) scanner including a plurality of detector units is provided. The method may be implemented on a computing device having at least one processor and at least one non-transitory storage medium. For each of the plurality of detector units, the method may include determining, based on scan data of one or more scans of a phantom at a plurality of positions, a first sum of coincidence events detected by the detector unit. The method may further include determining a second sum of coincidence events that are expected to be detected by the detector unit and determining, based on the first sum of coincidence events and the second sum of coincidence events, at least one correction parameter associated with the detector unit. The phantom may be moved to the plurality of positions along an axis of a field of view of the PET scanner during the one or more scans, and a length of the phantom may be less than a length of the field of view of the PET scanner along the axis.

According to yet another aspect of the present disclosure, a non-transitory computer readable medium is provided. The non-transitory computer readable medium may include at least one set of instructions. When executed by at least one processor of a computing device, the at least one set of instructions may direct the at least one processor to perform operations including: for each of the plurality of detector units, determining, based on scan data of one or more scans of a phantom at a plurality of positions, a first sum of coincidence events detected by the detector unit; determining a second sum of coincidence events that are expected to be detected by the detector unit; and determining, based on the first sum of coincidence events and the second sum of coincidence events, at least one correction parameter associated with the detector unit. The phantom may be moved to the plurality of positions along an axis of a field of view of the PET scanner during the one or more scans, and a length of the phantom may be less than a length of the field of view of the PET scanner along the axis Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 8 is a flowchart illustrating an exemplary process for determining a reference sum of coincidence events according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
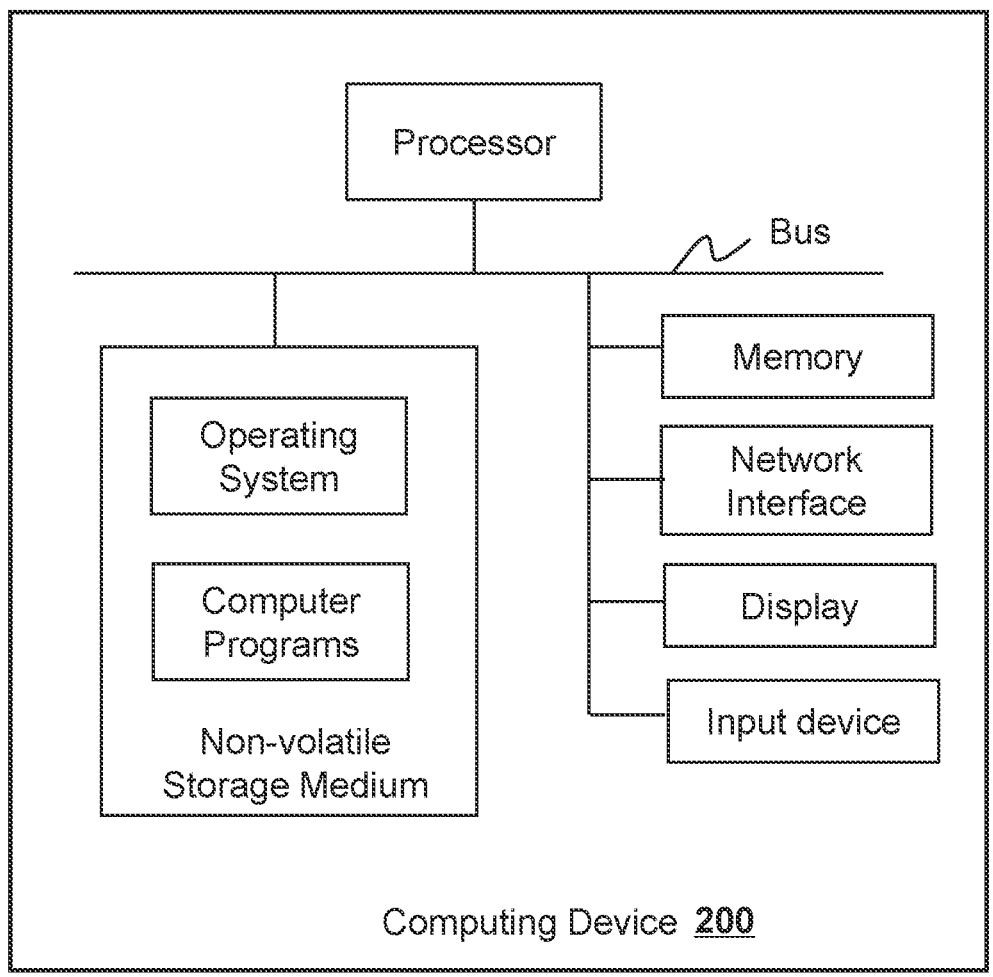
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for an imaging system. In some embodiments, the imaging system may include a single modality imaging system and/or a multi-modality imaging system. The single modality imaging system may include, for example, a PET system, a SPECT system, or the like, or any combination thereof. The multi-modality imaging system may include, for example, a positron emission tomography-X-ray imaging (PET-X-ray) system, a single-photon emission computed tomography-magnetic resonance imaging (SPECT-MRI) system, a positron emission tomography-computed tomography (PET-CT) system, a digital subtraction angiography-magnetic resonance imaging (DSA-MRI) system, etc. It should be noted that the imaging system described below is merely provided for illustration purposes, and not intended to limit the scope of the present disclosure.

The present disclosure provides mechanisms (which can include methods, systems, a computer-readable medium, etc.) for determining at least one correction parameter for a PET scanner. A phantom may be caused to move along the long axis of the FOV of a PET scanner in a specific manner. For example, the phantom may be moved to a plurality of positions at predetermined time intervals or continuously moved to the plurality of positions. Such a method may allow a phantom having a length that is less than the length of the FOV along the long axis of the FOV to be used to cover the whole FOV by moving the phantom. Thus, as compared to using a long phantom whose length is the same as or close to the length of the FOV, the systems and methods provided by the present disclosure involving a relatively short phantom may be more convenient in terms of transportation, storage, and/or and maneuver. Moreover, the cost of manufacturing such a relatively short phantom may also be reduced. For determining the at least one correction parameter for each detector unit of the PET scanner, an actual sum of coincidence events (also referred to as a first sum of coincidence events) that are detected by the detector unit may be determined based on scan data of the phantom. A reference sum of coincidence events (also referred to as a second sum of coincidence events) that are expected to be detected by the detector unit under ideal conditions may also be determined. The at least one correction parameter may be determined based on the actual sum of coincidence events and the reference sum of coincidence events. For example, the at least one correction parameter may include an axial block profile, a transverse block profile, a plane efficiency, a crystal efficiency, or the like, or any combination thereof.

Figure 1:
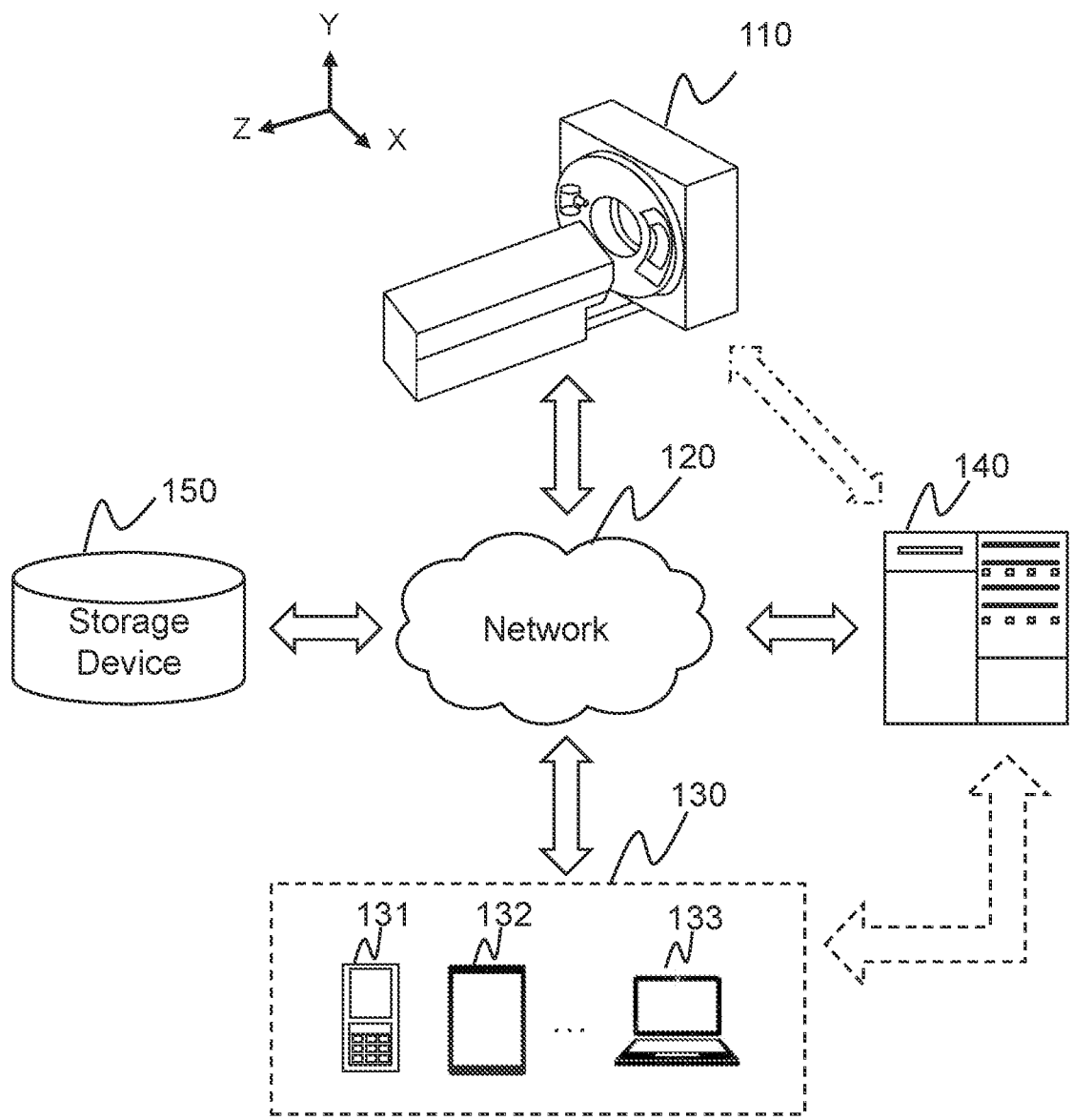
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include a imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via the network 120. The connection between the components of the imaging system 100 may be variable. Merely by way of example, the imaging device 110 may be connected to the processing device 140 through the network 120, as illustrated in FIG. 1. As another example, the imaging device 110 may be connected to the processing device 140 directly. As a further example, a terminal 130 may be connected to the processing device 140 through the network 120, as illustrated in FIG. 1, or connected to the processing device 140 directly.

The scanner (or referred to as the imaging device) 110 may generate or provide image data via scanning a subject (e.g., a patient) disposed on a scanning couch of the imaging device 110. In some embodiments, the imaging device 110 may be a Positron Emission Tomography (PET) device, a Single Photon Emission Computed Tomography (SPECT)

device, a Positron Emission Tomography-Computed Tomography (PET-CT) device, a Single Photon Emission Computed Tomography-Magnetic Resonance Imaging (SPECT-MRI) system, etc. In some embodiments, the subject may include a body, a substance, an object, or the like, or a combination thereof. In some embodiments, the subject may include a specific portion of a body, such as the head, the thorax, the abdomen, or the like, or a combination thereof. In some embodiments, the subject may include a specific organ or region of interest, such as an esophagus, a trachea, a bronchus, the stomach, the gallbladder, the small intestine, the colon, the bladder, the ureter, the uterus, a fallopian tube, etc.

In some embodiments, the imaging device 110 may include a gantry, a detector, an electronics module, a couch, and/or other components not shown, for example, a cooling assembly. The imaging device 110 may scan a subject and obtain information related to the subject. The gantry may support components (e.g., the detectors) for detecting radiation events to generate an image. The couch may position a subject in a detection region. The detector may detect radiation events (e.g., gamma photons) emitted from the detection region. In some embodiments, the detector may include a plurality of detector units. For example, a detector unit may be a block including four photomultiplier tubes with a square of sixty-four crystals. The detector units may be implemented in a suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. The electronics module may collect and/or process electrical signals (e.g., scintillation pulses) generated by the detector. The electronics module may include an adder, a multiplier, a subtracter, an amplifier, a drive circuit, a differential circuit, an integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof. In some embodiments, the detected radiation events may be stored or archived in a storage (e.g., the storage device 150), displayed on a display (e.g., a screen on a computing device), or transferred to a connected device (e.g., an external database). In some embodiments, a user may control the imaging device 110 via the terminal device 130.

The network 120 may include any suitable network that can facilitate the exchange of information and/or data for the imaging system 100. In some embodiments, one or more components of the imaging system 100 (e.g., the imaging device 110, the processing device 140, the storage device 150, the terminal(s) 130) may communicate information and/or data with one or more other components of the imaging system 100 via the network 120. For example, the processing device 140 may obtain image data from the imaging device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing device 140, and/or the storage device 150. For example, the terminal(s) 130 may obtain a processed image from the processing device 140. As another example, the terminal(s) 130 may obtain image data acquired via the imaging device 110 and transmit the image data to the processing device 140 to be processed. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to the processing device 140 via, for example, a bus, for further processing. Other types of input devices may include a cursor control device, such as a mouse, a trackball, or cursor direction keys, etc. The output device may include a display, a speaker, a printer, or the like, or a combination thereof. In some embodiments, the terminal(s) 130 may be part of the processing device 140.

In some embodiments, the terminal(s) 130 may send and/or receive image data for image reconstruction to/from the processing device 140 via a user interface. The user interface may be in the form of an application for image reconstruction implemented on the terminal(s) 130. The user interface implemented on the terminal(s) 130 may be configured to facilitate communication between a user and the processing device 140. In some embodiments, a user may input a request for determining at least one correction parameter via the user interface implemented on the terminal(s) 130. In some embodiments, the terminal(s) 130 may send the request for determining the at least one correction parameter to the processing device 140 for reconstructing an image based on a plurality of target input functions as described elsewhere in the present disclosure (e.g., FIGS. 6-9 and the descriptions thereof).

The storage device 150 may store data, instructions, and/or any other information. In some embodiments, the storage device 150 may store data obtained from the processing device 140, the terminal(s) 130, and/or the imaging device 110. For example, the storage device 150 may store scan data obtained from the imaging device 110. As another example, the storage device 150 may store one or more reconstructed images. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be part of the processing device 140.

In some embodiments, a three-dimensional coordinate system may be used in the imaging system 100 as illustrated in FIG. 1. A first axis may be parallel to the lateral direction of the couch (e.g., the X direction perpendicular to and pointing out of the paper as shown in FIG. 1). A second axis may be parallel to the longitudinal direction of the couch (e.g., the Z direction as shown in FIG. 1). The Z direction is also parallel to a long axis of the FOV of the imaging device 110. A third axis may be along a vertical direction of the couch (e.g., the Y direction as shown in FIG. 1). The origin of the three-dimensional coordinate system may be any point in the space. The origin of the three-dimensional coordinate system may be determined by an operator. The origin of the three-dimensional coordinate system may be determined by the imaging system 100.

The above description for FIG. 1 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

FIG. 2 is a schematic diagram illustrating exemplary hardware and/or software components of an exemplary computing device. In some embodiments, the processing device 140 may be implemented on the computing device 200. As illustrated in FIG. 2, the computing device 200 may include a processor and a storage connected through a bus. Computer programs may be stored in the storage (e.g., a non-volatile storage device). When the processor executes the computer programs, the processor may execute a method which will be described in connection with, for example, FIGS. 6-9. Optionally, the computing device may further include a network interface, a display, and an input device. The processor may be used to provide computing capabilities and generate controlling signals for controlling other components of the imaging system 100. The storage of the computing device may include a non-volatile storage medium and a memory. The non-volatile storage medium may store an operating system and computer programs. The memory may be used for executing the operating system and computer programs in the non-volatile storage medium. The network interface of the computing device may be used to communicate with an external terminal through a network connection.

The processor may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor may process image data obtained from the imaging device 110, the terminals 130, the storage device 150, and/or any other component of the imaging system 100. In some embodiments, the processor may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation s A and B).

The storage may store data/information obtained from the imaging device 110, the terminals 130, the storage device 150, and/or any other component of the imaging system 100. In some embodiments, the storage may include a mass storage device, a removable storage device, a volatile read-and-write memory, a read-only memory (ROM), or the like, or any combination thereof. For example, the mass storage may include a magnetic disk, an optical disk, solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage may store one or more programs and/or instructions to perform exemplary methods described in the present disclosure. For example, the storage may store a program for the processing device 140 for determining the position of a target region of a subject (e.g., a target portion of a patient).

The input device may be used to input signals, data, information, etc. In some embodiments, the input device may enable user interaction with the computing device 200. Examples of the input device may include a keyboard, a mouse, a touch screen, a microphone, or the like, or a combination thereof. Examples of the display may include a liquid crystal display (LCD), a light-emitting diode (LED)-based display, a flat panel display, a curved screen, a television device, a cathode ray tube (CRT), a touch screen, or the like, or a combination thereof.

The network interface may be connected to a network (e.g., the network 120) to facilitate data communications. For example, the network interface may establish connections between the processing device 140 and the imaging device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the network interface may be and/or include a standardized communication port, such as RS232, RS485, etc. In some embodiments, the network interface may be a specially designed communication port. For example, the network interface may be designed in accordance with the digital imaging and communications in medicine (DICOM) protocol.

It should be noted that the methods for determining at least one correction parameter provided in the present disclosure may be implemented on a PET scanner correction apparatus. The PET scanner correction apparatus may be implemented as part or all of the computing device 200 through software, hardware, or a combination thereof. In the following description, as an example for description, the methods are implemented on the computing device 200.

Figure 3:
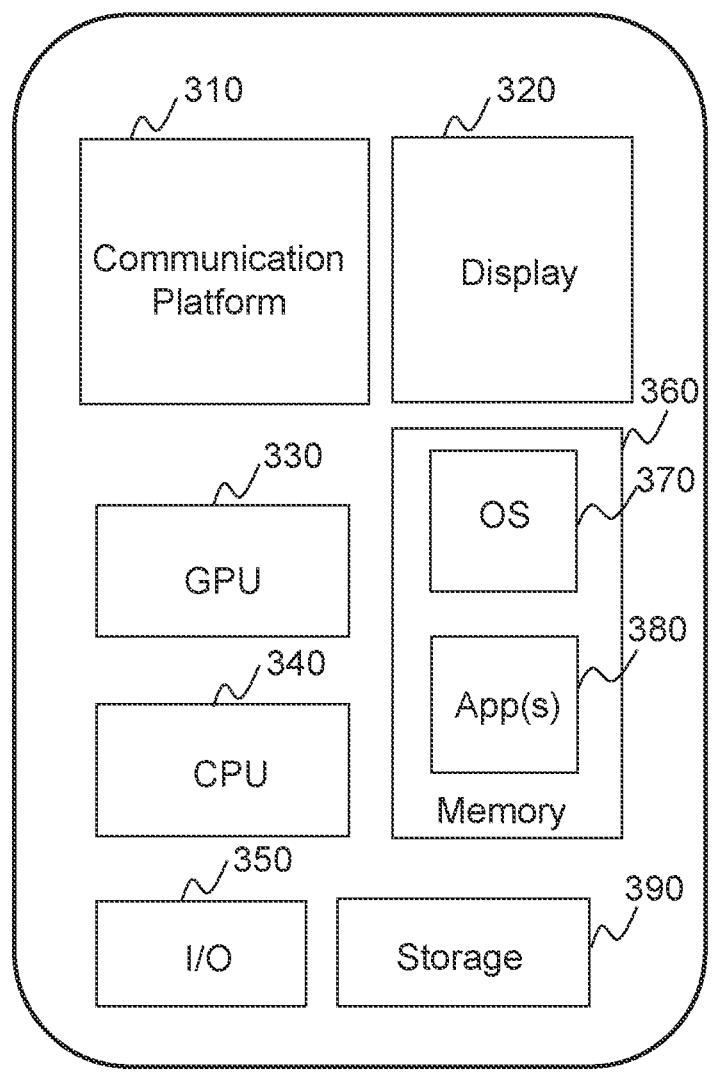
FIG. 3 is a schematic diagram illustrating exemplary hardware and/or software components of an exemplary terminal device according to some embodiments of the present disclosure.

FIG. 3 is a schematic diagram illustrating exemplary hardware and/or software components of an exemplary terminal device 300 according to some embodiments of the present disclosure. As illustrated in FIG. 3, the terminal device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the terminal device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
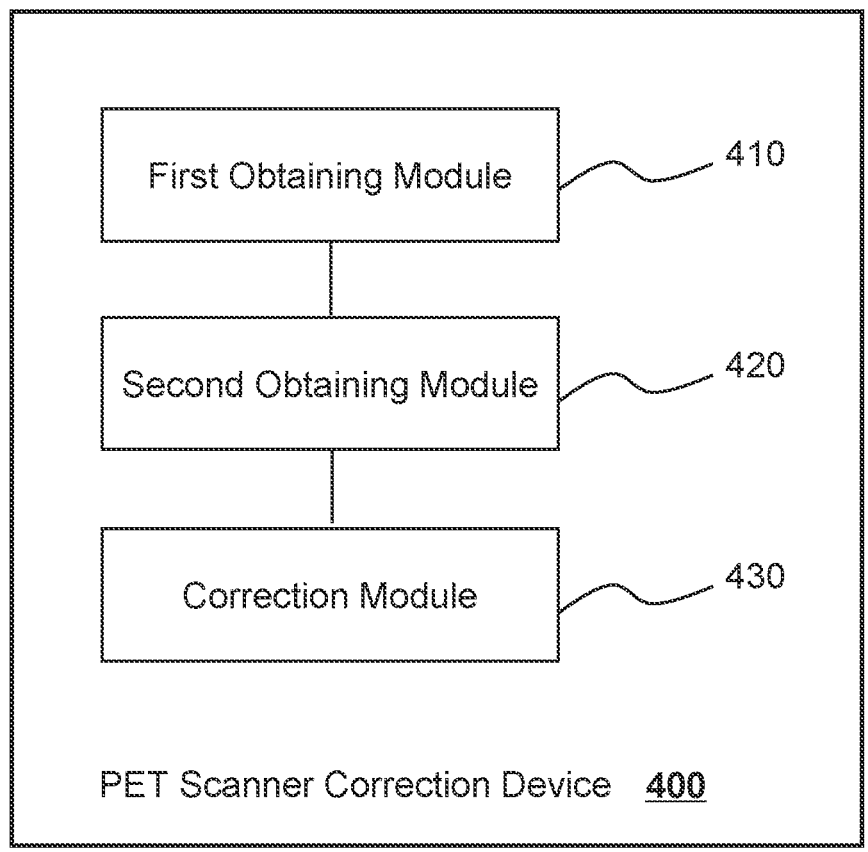
FIG. 4 is a block diagram illustrating an exemplary PET scanner correction device according to some embodiments of the present disclosure.

FIG. 4 is a block diagram illustrating an exemplary PET scanner correction device according to some embodiments of the present disclosure. As illustrated in FIG. 4, the PET scanner correction device 400 may include a first obtaining module 410, a second obtaining module 420, and a correction module 430. The modules may be hardware circuits of all or part of the processing device 140. The modules may also be implemented as an application or set of instructions read and executed by the processing device 140. Further, the modules may be any combination of the hardware circuits and the application/instructions. For example, the modules may be part of the processing device 140 when the processing device 140 is executing the application/set of instructions.

The first obtaining module 410 may obtain, for each of the plurality of detector units of the imaging device 110, an actual sum of coincidence events. The actual sum of coincidence events (also referred to as a first sum of coincidence events) may be determined based on scan data of one or more scans of a phantom at a plurality of positions.

The second obtaining module 420 may obtain, for each of the plurality of detector units of the imaging device 110, a reference sum of coincidence events. In some embodiments, the reference sum of coincidence events (also referred to as a second sum of coincidence events) may represent an expected sum of coincidence events under an ideal condition. As used herein, the "ideal condition" refers to a condition that each gamma photon emitted from the phantom is measured by the detector of the PET scanner. In some embodiments, for each of the plurality of positions, a count of coincidence events may be determined based on geometric parameters of the phantom, position information of the phantom, a scanning period of the phantom at the position, and information regarding the tracer (e.g., a concentration, a half-life period). The reference sum of coincidence events may be determined based on the count of coincidence events for each of the plurality of positions.

The correction module 430 may determine, for each of the plurality of detector units of the imaging device 110, at least one correction parameter. In some embodiments, the at least one correction parameter may be determined based on the actual sum of coincidence events and the reference sum of coincidence events. For example, the at least one correction parameter may include an axial block profile, a transverse block profile, a plane efficiency, a crystal efficiency, or the like, or any combination thereof. The detector of the PET scanner may include a plurality of detector units. A detector unit may be a block including multiple photomultiplier tubes with multiple crystals. In some embodiments, the at least one correction parameter may be determined based on a ratio of the actual sum of coincidence events to the reference sum of coincidence events. In some embodiments, the at least one correction parameter may be determined based on a ratio of the reference sum of coincidence events to the actual sum of coincidence events. In some embodiments, after a correction parameter is determined, a corrected actual sum of coincidence events may be generated using the correction parameter. The corrected actual sum of coincidence events may be used for determining another correction parameter.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the processing device 140 may include one or more additional modules. For example, the processing device 140 may further include a control module configured to control the movement of the phantom.

Figure 5:
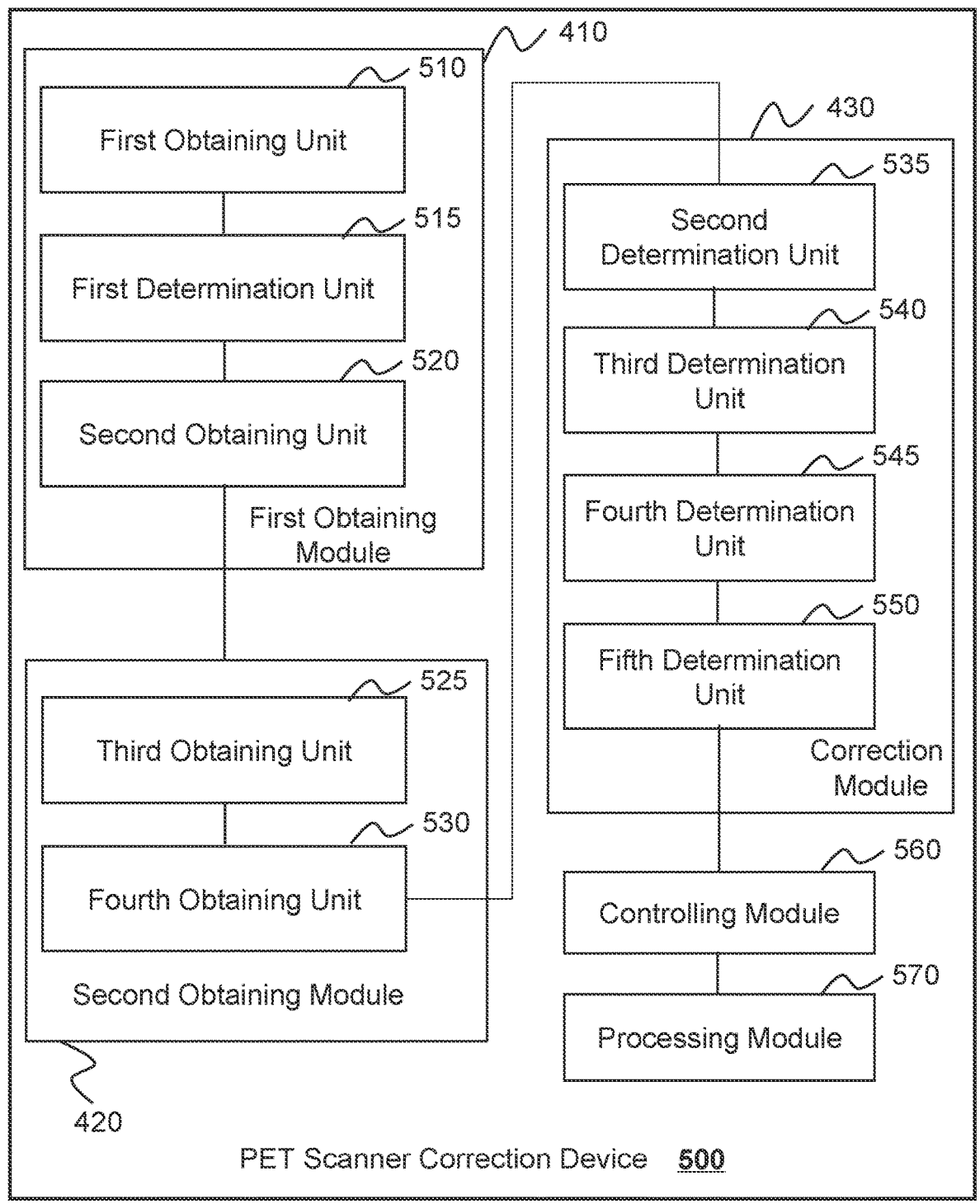
FIG. 5 is a block diagram illustrating an exemplary PET scanner correction device according to some embodiments of the present disclosure.

FIG. 5 is a block diagram illustrating an exemplary PET scanner correction device according to some embodiments of the present disclosure. The modules may be hardware circuits of all or part of the processing device 140. The modules may also be implemented as an application or set of instructions read and executed by the processing device 140. Further, the modules may be any combination of the hardware circuits and the application/instructions. For example, the modules may be part of the processing device 140 when the processing device 140 is executing the application/set of instructions.

As illustrated in FIG. 5, the first obtaining module 410 may include a first obtaining unit 510, a first determination unit 515, and a second obtaining unit 520. In some embodiments, the first obtaining unit 510 may obtain scan data of one or more scans of the phantom at a plurality of positions acquired by the detector. In some embodiments, the first determination unit 515 may determine, for each of the plurality of positions, an actual count of coincidence events.

In some embodiments, the PET scanner correction device 500 may further include a processing module 570. Before determining the actual count of coincidence events for each of the plurality of positions, the processing module 570 can perform one or more corrections on the scan data of the phantom at the plurality of positions to obtain corrected scan data. The actual count of coincidence events may be determined based on the corrected scan data by the first determination unit 515. The one or more corrections may include at least one of an attenuation correction, a dead-time correction, a random coincidence correction, a scatter correction, or the like, or any combination thereof. In some embodiments, a Computed Tomography (CT) scan may be performed on the phantom for generating a CT image of the phantom. An image registration operation may be executed to align the CT image with each of the plurality of positions. At least one of the one or more corrections, such as the attenuation correction, may be performed based on the CT image and the scan data.

The second obtaining module 420 may include a third obtaining unit 525 and a fourth obtaining unit 530. In some embodiments, the third obtaining unit 525 may determine, for each of the plurality of positions, a count of coincidence events based on geometric parameters of the phantom, position information of the phantom, a scanning period of the phantom at the position, and information regarding the tracer. The fourth obtaining unit 530 may determine the reference sum of coincidence events based on the count of coincidence events for each of the plurality of positions.

The correction module 430 may include a second determination unit 535, a third determination unit 540, a fourth determination unit 545, and a fifth determination unit 550. The second determination unit 535 may determine the axial block profile based on the actual sum of coincidence events (i.e., the first sum of coincidence events) and the reference sum of coincidence events (i.e., the second sum of coincidence events). The third determination unit 540 may determine a first corrected sum of coincidence events by correcting the first sum of coincidence events using the axial block profile and determining the plane efficiency based on the first corrected sum of coincidence events and the reference sum of coincidence events. The fourth determination unit 545 may determine a second corrected sum of coincidence events by correcting the first corrected sum of coincidence events using the plane efficiency and determining the transverse block profile determined based on the second corrected sum of coincidence events and the reference sum of coincidence events. The fifth determination unit 550 may determine a third corrected sum of coincidence events by correcting the second corrected sum of coincidence events using the transverse block profile and determining the crystal efficiency based on the third corrected sum of coincidence events and the reference sum of coincidence events.

In some embodiments, the PET scanner correction device 500 may further include a controlling module 560. The controlling module 560 may control the movement of the phantom along the long axis of the FOV of the PET scanner. For example, the controlling module 560 may control the couch of the PET scanner to move, thereby causing the position of the phantom with respect to the FOV of the PET scanner to be changed.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, any module mentioned above may be divided into two or more units. In some embodiments, the processing device 140 may include one or more additional modules. For example, the processing device 140 may further include a transmission module configured to transmit data (e.g., the at least one correction parameter) for one or more components in the imaging system 100.

Figure 6:
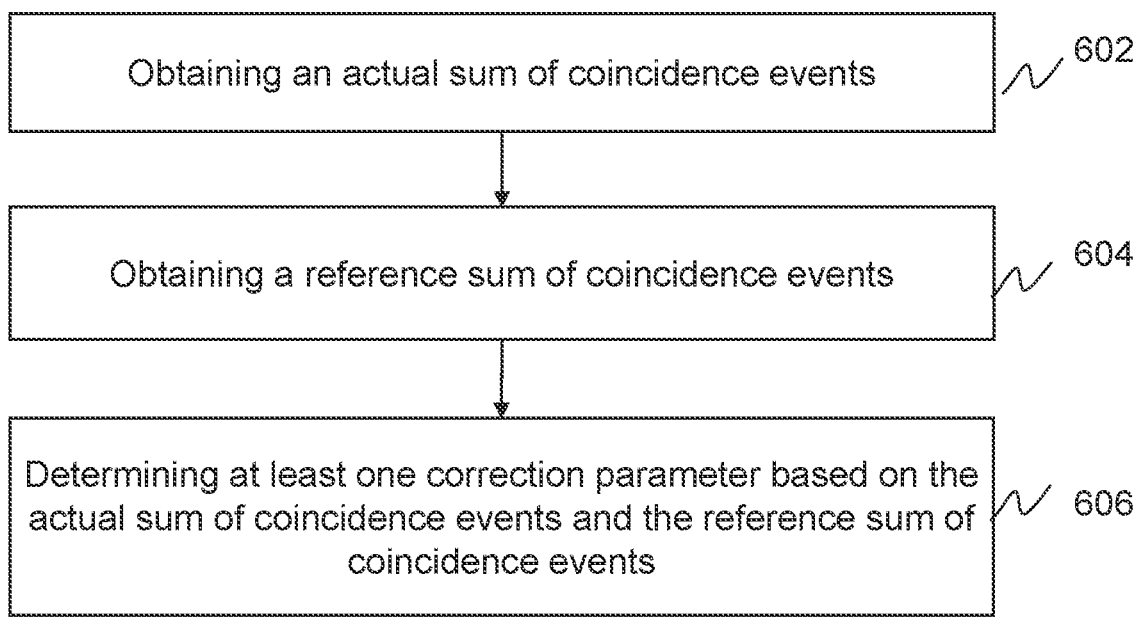
FIG. 6 is a flowchart illustrating an exemplary process for determining at least one correction parameter according to some embodiments of the present disclosure.

FIG. 6 is a flowchart illustrating an exemplary process for determining at least one correction parameter according to some embodiments of the present disclosure. In some embodiments, the imaging device 110 (such as a PET scanner) may include a plurality of detector units. The process 600 may be performed to determine the at least one correction parameter for each of the plurality of detector units. At least a portion of process 600 may be implemented on the computing device 200 as illustrated in FIG. 2, the terminal device 300 as illustrated in FIG. 3, and/or the PET scanner correction device 400 as illustrated in FIG. 4. In some embodiments, one or more operations of the process 600 may be implemented in the imaging system 100 as illustrated in FIG. 1. In some embodiments, one or more operations in the process 600 may be stored in the storage device 150 and/or the storage of the computing device 200 (e.g., an ROM, an RAM, etc.) in the form of instructions, and invoked and/or executed by the processing device 140, or the processor of the computing device 200. In some embodiments, the instructions may be transmitted to one or more components of the system 100 in the form of electronic current or electrical signals.

In 602, an actual sum of coincidence events may be obtained. In some embodiments, the first obtaining module 410 may perform operation 602 for each of the plurality of detector units of the PET scanner. For each of the plurality of detector units, the actual sum of coincidence events (also referred to as a first sum of coincidence events) that are detected by the detector unit may be determined based on scan data of one or more scans of a phantom at a plurality of positions.

In some embodiments, the length of the phantom may be less than the length of the FOV of the PET scanner along the long axis of the FOV (the Z direction as illustrated in FIG. 1). For brevity, the long axis of the FOV of the PET scanner may be referred to as the axis, unless otherwise stated. The phantom may have a cavity. The cavity may contain a PET tracer (e.g., in the form of a tracer solution), which may be used as a radiation source. The phantom may be placed in the FOV (e.g., placed on the couch of the PET scanner) and moved along the axis of the FOV. In some embodiments, the phantom may be fixed on the couch and caused to move by the movement of the couch. In some embodiments, the phantom may be caused to move by other movement controlling devices. For instance, the phantom may be driven by a motor to move along a sliding rail mounted on the top of the couch.

In some embodiments, the phantom may move discontinuously to the plurality of positions, for example, at predetermined time intervals. Multiple scans may be performed on the phantom at different positions. Merely by way of example, the phantom may move in a step-wise mode. For instance, the phantom may be moved to a first position of the plurality of positions and pause at the first position. A scan may be performed on the phantom at the first position. Then the phantom may be moved to a second position of the plurality of positions and pause at the second position. Another scan may be performed on the phantom at the second position. In some embodiments, the distance between two neighboring positions next to each other along the axis of the FOV may vary. As used herein, two positions where the phantom pauses and scans are performed are considered neighboring positions if they are next to each other along the axis of the FOV. In some embodiments, the distance between two neighboring positions may be a constant value.

A region that the phantom occupies in the FOV of the PET scanner at a position may be referred to as a sub-region of the FOV. As used herein, two sub-regions of the FOV where the phantom occupies are considered neighboring sub-regions if they are next to each other along the axis of the FOV. In some embodiments, at least two neighboring sub-regions of the FOV corresponding to two neighboring positions of the plurality of positions may overlap. For each movement, the phantom may be moved for a moving distance that is less than the length of the phantom. In some embodiments, at least two neighboring sub-regions of the FOV corresponding to neighboring positions of the plurality of positions do not overlap.

In some embodiments, the phantom may move continuously to a plurality of positions at varying speeds or a constant speed. A single scan may be performed on the phantom during the continuous movement of the phantom. For example, the phantom may move continuously at 3 millimeters (mm)/second (s), 5 mm/s, 8 mm/s, etc.

By the continuous or discontinuous movement of the phantom, the one or more scans of the phantom can cover the entire FOV of the PET scanner or a portion thereof. Thus, the scan data of the one or more scans may be used for determining at least one correction parameter associated with the PET scanner or the covered portion thereof.

As described in FIG. 1, the imaging system 100 may include the imaging device 110 (e.g., a PET scanner) and the processing device 140. The processing device 140 may be operably connected to the imaging device 110. The processing device 140 may obtain the scan data of the phantom at each position which is acquired by the PET scanner and then determine the actual sum of coincidence events. Optionally, the scan data of the phantom acquired by the PET scanner at each position may be stored in a storage device (e.g., the storage device 150 shown in FIG. 1). Alternatively or additionally, the scan data may be stored in the processing device 140 and/or the terminal device 130. In some embodiments, the scan data may be stored in the form of list mode data or sinogram data.

In 604, a reference sum of coincidence events may be obtained. In some embodiments, operation 604 may be performed by the second obtaining module 420. In some embodiments, the reference sum of coincidence events (also referred to as a second sum of coincidence events) may represent an expected sum of coincidence events that the detector unit is expected to detect under an ideal condition. As used herein, the "ideal condition" refers to a condition that each pair of gamma-photons emitted in a back-to-back manner due to the annihilation of positron-electron pairs without interacting with other substances and reach the detector surface are detected by the detector of the PET scanner. In some embodiments, for each of the plurality of positions, an expected count of coincidence events (also referred to as a second count of coincidence events) under the ideal condition may be determined based on geometric parameters of the phantom, position information of the phantom, a scanning period of the phantom at the position, and information regarding the tracer (e.g., a concentration, a half-life period). The reference sum of coincidence events may be determined based on the expected count of coincidence events for each of the plurality of positions.

In 606, at least one correction parameter may be determined based on the actual sum of coincidence events and the reference sum of coincidence events. In some embodiments, operation 606 may be performed by the correction module 430. The at least one correction parameter may be used for correcting the detecting efficiency for each of the plurality of detector units of the PET scanner. For example, the at least one correction parameter may include an axial block profile, a transverse block profile, a plane efficiency, a crystal efficiency, or the like, or any combination thereof. The detector of the PET scanner may include a plurality of detector units. The axial block profile and the transverse block profile may be used for compensating for the sensitivity distribution caused by the position inside the block detector (e.g., due to the gap between two neighbouring blocks). The plane efficiency may be used for compensating for the sensitivity distribution caused by the incident angle of the photon with respect to the surface of the detector (e.g., due to an incident angle other than 90° to the surface of the detector on which the photon impinges). The crystal efficiency may be used for compensating for the sensitivity distribution caused by differences in the properties of the detector crystals (e.g., due to impurities or non-uniformity of the crystals). In some embodiments, the at least one correction parameter may be determined based on a ratio of the actual sum of coincidence events to the reference sum of coincidence events. In some embodiments, the at least one correction parameter may be determined based on a ratio of the reference sum of coincidence events to the actual sum of coincidence events. In some embodiments, after a correction parameter is determined, a corrected actual sum of coincidence events may be generated using the correction parameter. The corrected actual sum of coincidence events may be used for determining another correction parameter. More description regarding the determination of the at least one correction parameter may be found elsewhere in the present disclosure, for example, in FIG. 9 and the description thereof.

In some embodiments, after a PET scan is performed on a subject (e.g., a patient, an animal), or a portion thereof, scan data of the scan may be corrected using the at least one correction parameter. A PET image may be reconstructed based on the corrected scan data. The correction using the at least one correction parameter may improve the quality of the PET image and provide more accurate information associated with the subject.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 7:
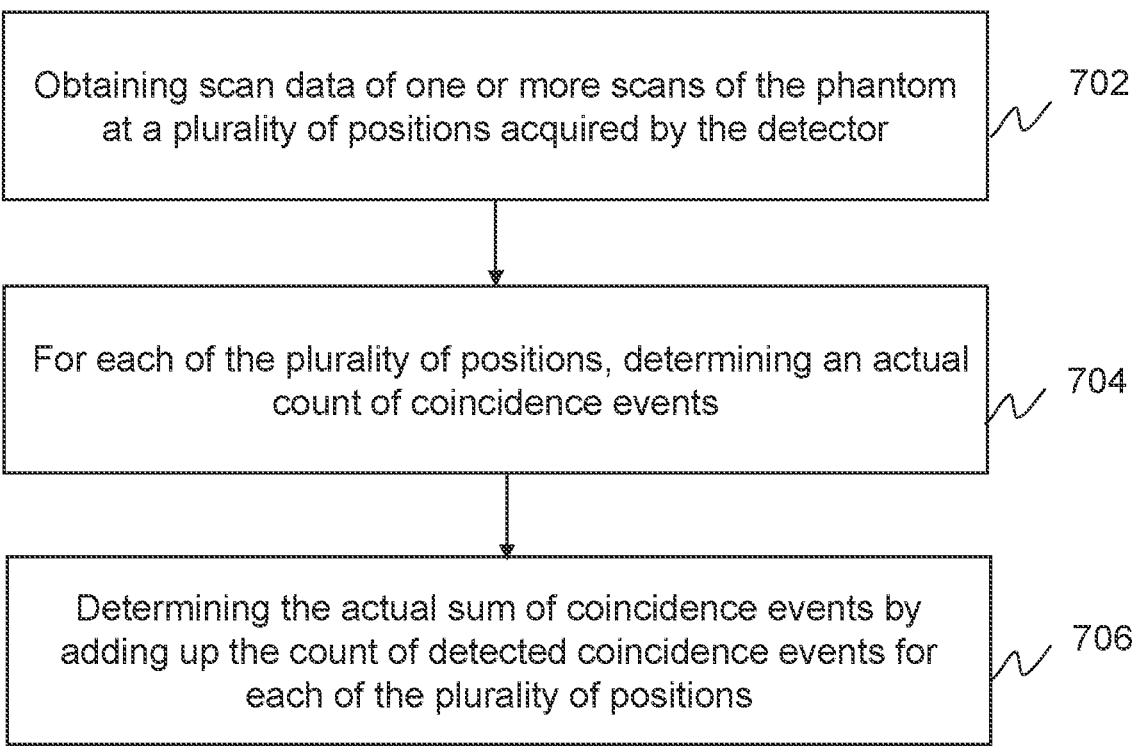
FIG. 7 a flowchart illustrating an exemplary process for determining an actual sum of coincidence events according to some embodiments of the present disclosure.

FIG. 7 is a flowchart illustrating an exemplary process for determining an actual sum of coincidence events according to some embodiments of the present disclosure. At least a portion of process 700 may be implemented on the computing device 200 as illustrated in FIG. 2, the terminal device 300 as illustrated in FIG. 3, and/or the PET scanner correction device 400 as illustrated in FIG. 4. In some embodiments, one or more operations of the process 700 may be implemented in the imaging system 100 as illustrated in FIG. 1. In some embodiments, one or more operations in the process 700 may be stored in the storage device 150 and/or the storage of the computing device 200 (e.g., an ROM, an RAM, etc.) in the form of instructions, and invoked and/or executed by the processing device 140, or the processor of the computing device 200. In some embodiments, the instructions may be transmitted to one or more components of the system 100 in the form of electronic current or electrical signals.

In 702, scan data of one or more scans of the phantom at a plurality of positions acquired by the detector are obtained. In some embodiments, operation 702 may be performed by the first obtaining unit 510 of the first obtaining module 410. In some embodiment, operation 702 may be performed in a similar manner as operation 602, the description of which is not repeated here.

In 704, for each of the plurality of positions, an actual count of coincidence events (also referred to as a first count of coincidence events) may be determined. In some embodiments, operation 704 may be performed by the first determination unit 515 of the first obtaining module 410. In some embodiments, before determining the actual count of coincidence events for each of the plurality of positions for the detector unit, the computing device 200 can perform one or more corrections on the scan data of the phantom at the plurality of positions to obtain corrected scan data. The actual count of coincidence events may be determined based on the corrected scan data. The one or more corrections may include at least one of an attenuation correction, a dead-time correction, a random coincidence correction, a scatter correction, or the like, or any combination thereof. In some embodiments, a Computed Tomography (CT) scan may be performed on the phantom for generating a CT image of the phantom. An image registration operation may be executed to align the CT image with each of the plurality of positions.

At least one of the one or more corrections, such as the attenuation correction, may be performed based on the CT image and the scan data.

In 706, the actual sum of coincidence events may be determined by adding up the count of coincidence events for each of the plurality of positions. In some embodiments, operation 706 may be performed by the second obtaining unit 520 of the first obtaining module 410. In some embodiments, the actual sum of coincidence events may be a weighted sum of the count of coincidence events for each of the plurality of positions. For instance, a weight of an oblique LOR may be higher than a weight of a vertical LOR. The angle between the vertical LOR and a pair of corresponding detector units may be 90°. The angle between the oblique LOR and a pair of corresponding detector units may be other than 90°. Since a pair of gamma photons relating to the oblique LOR may travel a longer distance to reach the detector as compared to the vertical LOR, assigning a higher weight to the oblique LOR may improve the accuracy of the determination of the actual sum of coincidence.

It should be noted that the above description regarding the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 8 is a flowchart illustrating an exemplary process for determining a reference sum of coincidence events according to some embodiments of the present disclosure. At least a portion of process 800 may be implemented on the computing device 200 as illustrated in FIG. 2, the terminal device 300 as illustrated in FIG. 3, and/or the PET scanner correction device 400 as illustrated in FIG. 4. In some embodiments, one or more operations of the process 800 may be implemented in the imaging system 100 as illustrated in FIG. 1. In some embodiments, one or more operations in the process 800 may be stored in the storage device 150 and/or the storage of the computing device 200 (e.g., an ROM, an RAM, etc.) in the form of instructions, and invoked and/or executed by the processing device 140, or the processor of the computing device 200. In some embodiments, the instructions may be transmitted to one or more components of the system 100 in the form of electronic current or electrical signals.

In 802, for each of the plurality of positions, an expected count of coincidence events may be determined based on geometric parameters of the phantom, position information of the phantom, and a scanning period of the phantom at the position. In some embodiments, other factors may also be considered when determining the expected count of coincidence events, such as information regarding the tracer. In some embodiments, the second obtaining module 420 (e.g., the third obtaining unit 525) may perform operation 802 for each of the plurality of detector units of the PET scanner. For example, the geometric parameters may include the shape and the dimensions of the phantom. The position information of the phantom may refer to a spatial location of the phantom relative to the gantry of the imaging system 100. For example, the position of the phantom may be described using the position of a central point of the phantom. In some embodiments, the position information of the phantom may be determined based on the couch position with respect to the PET scanner when the phantom is caused to move by the movement of the couch. In some embodiments, for a discontinuous movement of the phantom (that is, the phantom pauses after reaching one of the plurality of positions), the scanning period refers to a duration of a scan on the phantom at a position. In some embodiments, for a continuous movement of the phantom (that is, the phantom keeps moving without pausing at any one of the plurality of positions), the scanning period refers to an average duration of a portion of the scan on the phantom when the phantom is in the vicinity of the position.

In 804, the reference sum of coincidence events may be determined based on the expected count of coincidence events for each of the plurality of positions. In some embodiments, the second obtaining module 420 (e.g., the fourth obtaining unit 530) may perform operation 804 for each of the plurality of detector units of the PET scanner.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
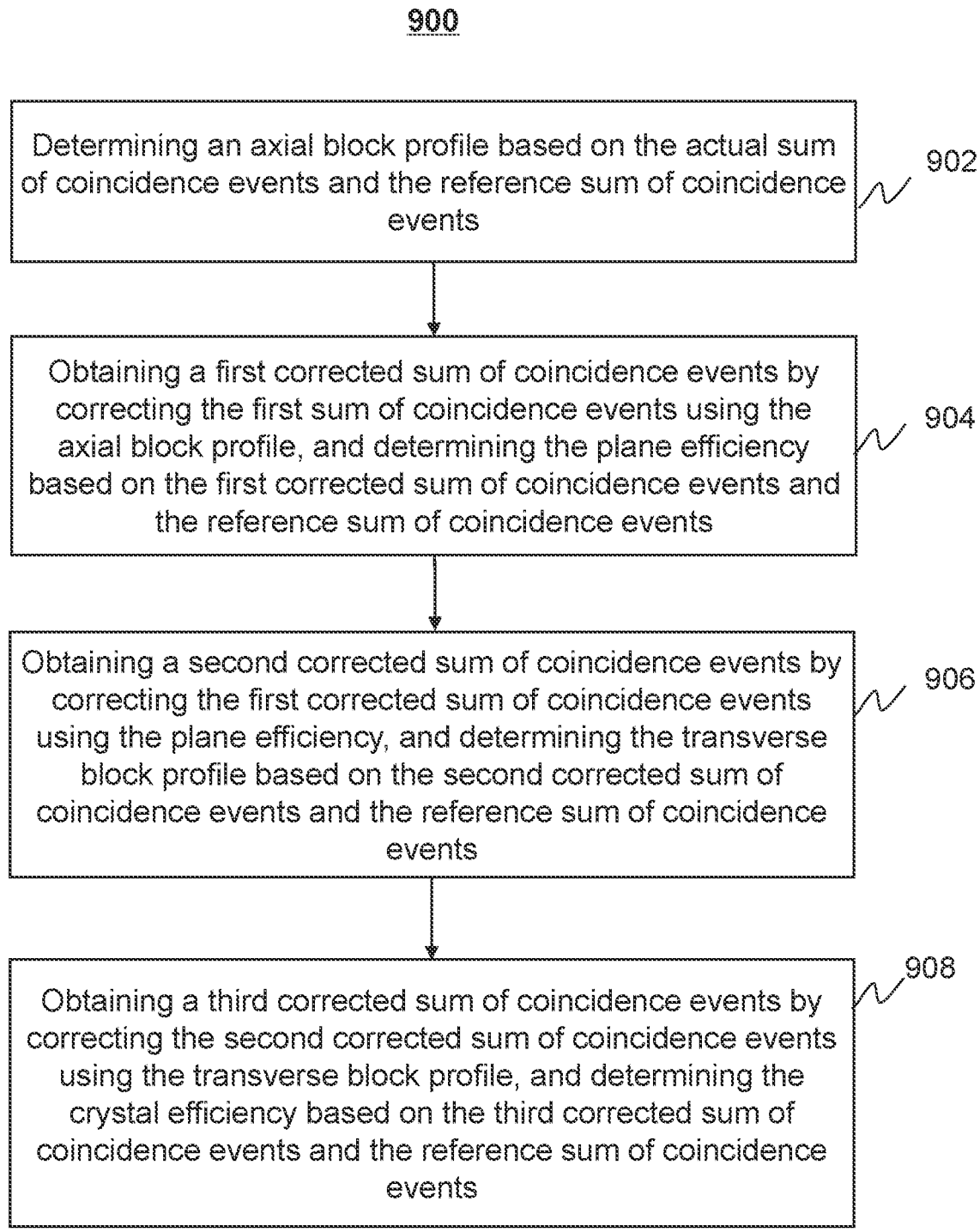
FIG. 9 is a flowchart illustrating an exemplary process for determining at least one correction parameter according to some embodiments of the present disclosure.

FIG. 9 is a flowchart illustrating an exemplary process for determining at least one correction parameter according to some embodiments of the present disclosure. In some embodiments, for each of the plurality of detector units of the PET scanner, the at least one correction parameter may be determined. At least a portion of process 900 may be implemented on the computing device 200 as illustrated in FIG. 2, the terminal device 300 as illustrated in FIG. 3, and/or the PET scanner correction device 400 as illustrated in FIG. 4. In some embodiments, one or more operations of the process 900 may be implemented in the imaging system 100 as illustrated in FIG. 1. In some embodiments, one or more operations in the process 900 may be stored in the storage device 150 and/or the storage of the computing device 200 (e.g., an ROM, an RAM, etc.) in the form of instructions, and invoked and/or executed by the processing device 140, or the processor of the computing device 200. In some embodiments, the instructions may be transmitted to one or more components of the system 100 in the form of electronic current or electrical signals.

In 902, an axial block profile may be determined based on the actual sum of coincidence events (i.e., the first sum of coincidence events) and the reference sum of coincidence events (i.e., the second sum of coincidence events). In some embodiments, operation 902 may be performed by the correction module 430 (e.g., the second determination unit 535). In some embodiments, the axial block profile may be determined based on a ratio of the actual sum of coincidence events to the reference sum of coincidence events. In some embodiments, the axial block profile may be determined based on a ratio of the reference sum of coincidence events to the actual sum of coincidence events.

In 904, a first corrected sum of coincidence events may be obtained by correcting the first sum of coincidence events using the axial block profile, and the plane efficiency may be determined based on the first corrected sum of coincidence events and the reference sum of coincidence events. In some embodiments, operation 902 may be performed by the correction module 430 (e.g., the third determination unit 540). In some embodiments, to obtain the first corrected sum of coincidence events, the scan data may be transformed, for example, by decreasing one or more dimensions of the scan data to focus on the impact of the plane efficiency. In some embodiments, the plane efficiency may be determined based on a ratio of the first corrected sum of coincidence events to the reference sum of coincidence events. In some embodiments, the plane efficiency may be determined based on a ratio of the reference sum of coincidence events to the first corrected sum of coincidence events.

In 906, a second corrected sum of coincidence events may be obtained by correcting the first corrected sum of coincidence events using the plane efficiency, and the transverse block profile may be determined based on the second corrected sum of coincidence events and the reference sum of coincidence events. In some embodiments, operation 902 may be performed by the correction module 430 (e.g., the fourth determination unit 545). In some embodiments, to obtain the second corrected sum of coincidence events, the scan data may be transformed, for example, by decreasing one or more dimensions of the scan data to focus on the impact of the transverse block profile. In some embodiments, the transverse block profile may be determined based on a ratio of the second corrected sum of coincidence events to the reference sum of coincidence events. In some embodiments, the transverse block profile may be determined based on a ratio of the reference sum of coincidence events to the second corrected sum of coincidence events.

In 908, a third corrected sum of coincidence events may be obtained by correcting the second corrected sum of coincidence events using the transverse block profile, and the crystal efficiency may be determined based on the third corrected sum of coincidence events and the reference sum of coincidence events. In some embodiments, operation 902 may be performed by the correction module 430 (e.g., the fifth determination unit 550). In some embodiments, to obtain the third corrected sum of coincidence events, the scan data may be transformed, for example, by decreasing one or more dimensions of the scan data to focus on the impact of the crystal efficiency. In some embodiments, the crystal efficiency may be determined based on a ratio of the third corrected sum of coincidence events to the reference sum of coincidence events. In some embodiments, the crystal efficiency may be determined based on a ratio of the reference sum of coincidence events to the third corrected sum of coincidence events.

Such a process for determining the correction parameters may improve the accuracy of the correction parameters, and thus improving the quality of a PET image reconstructed using the correction parameters. It should be noted that the order for determining the correction parameters are not limited by the present disclosure. For example, the transverse block profile may be determined before the plane efficiency is determined. In some embodiments, the determination for one or more correction parameters may be omitted, such as the plane efficiency.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable media having computer-readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system for determining at least one correction parameter for a Positron Emission Tomography (PET) scanner including a plurality of detector units, comprising:
    at least one non-transitory storage medium including a set of instructions; and
    at least one processor in communication with the at least one non-transitory storage medium, wherein when executing the set of instructions, the at least one processor is configured to cause the system to perform operations including:
        for each of the plurality of detector units,
            determining, based on scan data of one or more scans of a phantom at a plurality of positions, a first sum of coincidence events detected by the detector unit, wherein the phantom is moved to the plurality of positions along an axis of a field of view of the PET scanner during the one or more scans, and a length of the phantom is less than a length of the field of view of the PET scanner along the axis;
            determining a second sum of coincidence events that are expected to be detected by the detector unit; and
            determining, based on the first sum of coincidence events and the second sum of coincidence events, at least one correction parameter associated with the detector unit.

2. The system of claim 1, wherein to determine the first sum of coincidence events, the at least one processor is configured to cause the system to perform operations including:
    obtaining the scan data of the one or more scans of the phantom at the plurality of positions;
    for each of the plurality of positions,
        determining, based on the scan data, a first count of detected coincidence events that are detected by the detector unit; and
    determining the first sum of coincidence events based on the first count of detected coincidence events for each of the plurality of positions.

3. The system of claim 1, wherein to determine the second sum of coincidence events, the at least one processor is configured to cause the system to perform operations including:
    for each of the plurality of positions,
        determining a second count of coincidence events that are expected to be detected by the detector unit based on geometric parameters of the phantom, position information of the phantom, and a scanning period of the phantom at the position; and determining the second sum of coincidence events based on the second count of coincidence events for each of the plurality of positions.

4. The system of claim 1, wherein the phantom is moved to the plurality of positions in a step-wise mode, and a moving distance for each movement of the phantom is less than the length of the phantom.

5. The system of claim 1, wherein the phantom is continuously moved to the plurality of positions.

6. The system of claim 1, wherein to determine the first sum of coincidence events, the at least one processor is configured to cause the system to perform operations including:

performing one or more corrections on the scan data of the one or more scans of the phantom at the plurality of positions to obtain corrected scan data, wherein the one or more corrections include at least one of an attenuation correction, a dead-time correction, a random coincidence correction, or a scatter correction; and determining the first sum of coincidence events based on the corrected scan data.

7. The system of claim 1, wherein the at least one correction parameter includes an axial block profile, and to determine the at least one correction parameter, the at least one processor is configured to cause the system to perform operations including:

determining the axial block profile associated with the PET scanner based on the first sum of coincidence events and the second sum of coincidence events.

8. The system of claim 7, wherein the at least one correction parameter includes a plane efficiency, and to determine the at least one correction parameter, the at least one processor is configured to cause the system to perform operations including:

obtaining a first corrected sum of coincidence events by correcting the first sum of coincidence events using the axial block profile for each detector unit; and determining the plane efficiency associated with the PET scanner based on the first corrected sum of coincidence events and the second sum of coincidence events.

9. The system of claim 8, wherein the at least one correction parameter includes a transverse block profile, and to determine the at least one correction parameter, the at least one processor is further configured to cause the system to perform operations including:

obtaining a second corrected sum of coincidence events by correcting the first corrected sum of coincidence events using the plane efficiency for each detector unit; and determining the transverse block profile associated with the PET scanner based on the second corrected sum of coincidence events and the second sum of coincidence events.

10. The system of claim 9, wherein the at least one correction parameter includes a crystal efficiency, and to determine the at least one correction parameter, the at least one processor is configured to cause the system to perform operations including:

obtaining a third corrected sum of coincidence events by correcting the second corrected sum of coincidence events using the transverse block profile for each detector unit; and determining the crystal efficiency associated with the PET scanner based on the third corrected sum of coincidence events and the second sum of coincidence events.

11. A method for determining at least one correction parameter for a Positron Emission Tomography (PET) scanner including a plurality of detector units, implemented on a computing device having at least one processor and at least one non-transitory storage medium, the method comprising:

for each of the plurality of detector units, determining, based on scan data of one or more scans of a phantom at a plurality of positions, a first sum of coincidence events detected by the detector unit, wherein the phantom is moved to the plurality of positions along an axis of a field of view of the PET scanner during the one or more scans, and a length of the phantom is less than a length of the field of view of the PET scanner along the axis;

determining a second sum of coincidence events that are expected to be detected by the detector unit; and determining, based on the first sum of coincidence events and the second sum of coincidence events, at least one correction parameter associated with the detector unit.

12. The method of claim 11, wherein determining the first sum of coincidence events includes:

obtaining the scan data of the one or more scans of the phantom at the plurality of positions;

for each of the plurality of positions, determining, based on the scan data, a first count of detected coincidence events that are detected by the detector unit; and determining the first sum of coincidence events based on the first count of detected coincidence events for each of the plurality of positions.

13. The method of claim 11, wherein determining the second sum of coincidence events includes:

for each of the plurality of positions, determining a second count of coincidence events that are expected to be detected by the detector unit based on geometric parameters of the phantom, position information of the phantom, and a scanning period of the phantom at the position; and determining the second sum of coincidence events based on the second count of coincidence events for each of the plurality of positions.

14. The method of claim 11, wherein the phantom is moved to the plurality of positions in a step-wise mode, and a moving distance for each movement of the phantom is less than the length of the phantom.

15. The method of claim 11, wherein determining the first sum of coincidence events includes:

performing one or more corrections on the scan data of the one or more scans of the phantom at the plurality of positions to obtain corrected scan data, wherein the one or more corrections include at least one of an attenuation correction, a dead-time correction, a random coincidence correction, or a scatter correction; and determining the first sum of coincidence events based on the corrected scan data.

16. The method of claim 12, wherein the at least one correction parameter includes an axial block profile, and determining the at least one correction parameter includes:

determining the axial block profile associated with the PET scanner based on the first sum of coincidence events and the second sum of coincidence events.

17. The method of claim 16, wherein the at least one correction parameter includes a plane efficiency, and determining the at least one correction parameter further includes:

obtaining a first corrected sum of coincidence events by correcting the first sum of coincidence events using the axial block profile for each detector unit; and determining the plane efficiency associated with the PET scanner based on the first corrected sum of coincidence events and the second sum of coincidence events.

18. The method of claim 17, wherein the at least one correction parameter includes a transverse block profile, and determining the at least one correction parameter further includes:

obtaining a second corrected sum of coincidence events by correcting the first corrected sum of coincidence events using the plane efficiency for each detector unit; and determining the transverse block profile associated with the PET scanner based on the second corrected sum of coincidence events and the second sum of coincidence events.

19. The method of claim 18, wherein the at least one correction parameter includes a crystal efficiency, and determining the at least one correction parameter further includes:

obtaining a third corrected sum of coincidence events by correcting the second corrected sum of coincidence events using the transverse block profile for each detector unit; and determining the crystal efficiency associated with the PET scanner based on the third corrected sum of coincidence events and the second sum of coincidence events.

20. A non-transitory computer readable medium, comprising at least one set of instructions, wherein when executed by at least one processor of a computing device, the at least one set of instructions direct the at least one processor to perform operations including:

for each of the plurality of detector units, determining, based on scan data of one or more scans of a phantom at a plurality of positions, a first sum of coincidence events detected by the detector unit, wherein the phantom is moved to the plurality of positions along an axis of a field of view of the PET scanner during the one or more scans, and a length of the phantom is less than a length of the field of view of the PET scanner along the axis;

determining a second sum of coincidence events that are expected to be detected by the detector unit; and determining, based on the first sum of coincidence events and the second sum of coincidence events, at least one correction parameter associated with the detector unit.

* * * * *